US007173697B1

(12) United States Patent
Moosmüller et al.

(10) Patent No.: US 7,173,697 B1
(45) Date of Patent: Feb. 6, 2007

(54) LOW TRUNCATION LOSS, NON-RECIPROCAL NEPHELOMETER WITH INTEGRATING SPHERE

(76) Inventors: Hans Moosmüller, 4551 Lynnfield Ct., Reno, NV (US) 89509; Patrick W. Arnott, 4833 Ramcreek Trail, Reno, NV (US) 89509

( * ) Notice: Subject to any disclaimer, the term of this patent is extended or adjusted under 35 U.S.C. 154(b) by 0 days.

(21) Appl. No.: 11/259,934

(22) Filed: Oct. 26, 2005

Related U.S. Application Data

(63) Continuation-in-part of application No. 10/865,235, filed on Jun. 9, 2004.

(60) Provisional application No. 60/477,290, filed on Jun. 9, 2003.

(51) Int. Cl.
*G01N 15/02* (2006.01)
*G01J 1/04* (2006.01)
(52) U.S. Cl. .................... 356/338; 356/339; 356/236
(58) Field of Classification Search ............... None
See application file for complete search history.

(56) References Cited

U.S. PATENT DOCUMENTS

| 4,280,625 | A | * | 7/1981 | Grobbelaar et al. | ........ | 209/582 |
| 4,690,560 | A | * | 9/1987 | Coogan | ........ | 356/338 |
| 4,942,305 | A | * | 7/1990 | Sommer | ........ | 250/574 |
| 5,251,004 | A | * | 10/1993 | Doiron et al. | ........ | 356/236 |

OTHER PUBLICATIONS

N. C. Ahlquist, "A New Instrument for Evaluating the Visual Quality of Air," *Jr. Air Pollut. Control Assoc.*, vol. 17, pp. 467-469, 1967.

T. L. Anderson et al., "Performance Characteristics of a High-Sensitivity, Three-Wavelength, Total Scatter/Backscatter Nephelometer," *Jr. of Atmos. Oceanic Technol.*, vol. 13, pp. 967-986, 1996.

T. L. Anderson et al., "Determining Aerosol Radiative Properties Using the TSI 3563 Integrating Nephelometer," *Aerosol Sci. Tech.* vol. 29, pp. 57-69, Jul. 1998.

B. A. Bodhaine et al., "Three-Wavelength Nephelometer Suitable for Aircraft Measurement of Background Aerosol Scattering Coefficient," *Atmos. Enviro.*, vol. 25A, pp. 2267-2276, 1991.

R. G. Beuttell et al., "Instruments for the Measurement of the Visual Range," *Jr. od Sci. Instrum.*, vol. 26, pp. 357-359, Nov. 1949.

R. J. Charlson et al., "The Direct Measurement of Atmospheric Light Scattering Coefficient for Studies of Visibility and Pollution," *Atmos. Environ.* vol. 1, pp. 469-478, 1967.

(Continued)

*Primary Examiner*—Michael P. Stafira
(74) *Attorney, Agent, or Firm*—Sierra Patent Group, Ltd.

(57) ABSTRACT

A non-reciprocal nephelometer is disclosed herein that uses an integrating sphere with attached truncation-reduction tubes to contain the sample volume and to integrate the scattered light. The disclosed nephelometer improves on the imperfect angular response by using an integrating sphere design with forward (backward) truncation angles of $\approx 1°$ ($\approx 179°$), it reduces sampling losses by employing a substantially straight vertical flow path. In one disclosed embodiment, an illumination assembly consisting of one or multiple diffuse light sources is provided for homogenously illuminating the integrating sphere. An illumination aperture admits light from the light sources, a sensing aperture admits scattered light to an optical detector, and a dark aperture provides a dark background viewing area for the optical detector.

18 Claims, 4 Drawing Sheets

OTHER PUBLICATIONS

K. J. Deilamian et al., "Stray-Light Suppression wirh High-Collection Efficiency in Laser Light-Scattering Experiments," *Appl. Opt.*, vol. 31, pp. 2820-2824, 1992.

D. S. Ensor et al., "Angular Truncation Error in the Integrating-Nephelometer," *Atmos Environ.*, vol. 4, pp. 481-487, 1970.

W. B. Fussell, "Approximate Theory of the Integrating Sphere," *NBS Technical Note*, pp. 594-597, (year) 1974.

H. E. Gerber, "Portable Cell for Simultaneously Measuring the Coefficients of Light Scattering and Extinction for Ambient Aerosols", *Appl. Opt.*, vol. 18, pp. 1009-1014, 1979.

H. E. Gerber, "Simultaneous Measurements of Aerosol Scattering and Extinction Coefficients in a Multi-Pass Cell," *Light Absorption by Aerosol Particles*, Spectrum Press, Gerber and Hindeman eds., pp. 231-241, 1982.

H. Hasan et al., "Integrating Nephleometer Response Corrections for Bimodal Size Distributions," *Aersol Sci. Tech.*, vol. 2, pp. 443-453, 1983.

J. Heintzenberg et al, "The Angular Calibration of the Total Scatter/Backscatter Nephelometer, Consequences and Applications," *Staub-Reinhalt. Luft.* vol. 38, pp. 62-63, 1978.

J. Heintzenberg et al, "Design and Applications of the Integrating Nephelometer: A Review," *J. of Atmosph. Oceanic Technol.*, vol. 13, pp. 987-1000, 1996.

J. Heintzenberg et al, "Calculations on the Determination of the Scattering Coefficient of Turbid Air with Integrating Nephelometers," *Atmos. Environ.*, vol. 7, 509-519, 1973.

H. Horvath et al., "Calibration of Integrating Nephelometers in the Posr-Halocarbon Era," *Atmos. Environ.*, vol. 28, 1219-1223, 1973.

J. A. Jacquez et al., "Theory of the Integrating Sphere," *Jr. Opt. Soc. Am.*, vol. 45, pp. 460-470, 1955.

Author Anonymous, "A Guide to Integrating Sphere Photometry and Radiometry," Labsphere, Inc. 1994.

H. Moosmüler et al., "Equal Intensity and Phase Contours in Focused Faussian Laser Beams," *IEEE J. Quantum Elecron.*, vol. 27, pp. 869-887, 1991.

G. W. Mulholland, "Radiometric Model of the Transmission Cell-Reciprocal Nephelometer," *Atmos. Environ.*, vol. 28, pp. 873-887, 1994.

R. G. Pinnick et al., "Aersol in the Arid Southwestern United States: Measurements of Mass Loading, Volatility, Size distribution, Absorption Characteristics, Black Carbon Content, and Vertical Structure to 7 km Above Sea Level," *Jr. of Geophys. Res.*, vol. 98, pp. 2651-2666, 1993.

J. N. Porter et al., "Aerosol Size Distribution Models Based on in Situ Measurements," *Jr. of Geophys. Res.*, vol. 102, pp. 6035-6045, 1997.

H. Quenzel, "Der Einfluss der Aerosolgröβenverteilung auf die Messgenauigkeit von Streulichtmessern.," *Gerlands Beitr. Geophys.*, vol. 78, 251-264, 1969.

H. Quenzel et al., "Calculations about the Systematic error of Visibility-Meters Measuring Scattered Light," *Atmos. Environ.*, vol. 9, pp. 587-601, 1975.

R. A. Rabinoff et al., "Effect of Aersol Size Distribution on the Accuracy of the Integrating Nephelometer," *Jr. Appl. Meteor.*, vol. 12, pp. 184-186, 1973.

J. M. Rosen et al., "Nephelometer Optical Response Model for the Interpretation of Atmospheric Aersol Measurements," *Appl. Opt.* vol. 36, pp. 2642-2649, 1997.

R. Varma et al., "A New Integrating Nephelometer For Aerosol Light Scattering Studies," Abstract from the 21st Annual Conference of the American Association for Aerosol research, Charlotte, North Carolina, oct. 7-11, 2002.

R. Varma et al., "The New DRI Integrating Nephelometer," Power Point Presentation at the 21st Annual Conference of the American Association for Aerosol research, Charlotte, North Carolina, Oct. 7-11, 2002.

R. Varma et al., "Towards an Ideal Integratng Nephelometer," 12 pages submitted to *Opt. Letters,* on Dec. 4, 2002.

* cited by examiner

LOW TRUNCATION LOSS, NON-RECIPROCAL NEPHELOMETER WITH INTEGRATING SPHERE

CROSS-REFERENCE TO RELATED APPLICATIONS

This application is a continuation-in-part of U.S. patent application Ser. No. 10/865,235, filed Jun. 9, 2004, which claims priority to U.S. Provisional Patent Application Ser. No. 60/477,290, filed Jun. 9, 2003, which is incorporated by reference as if set forth herewith.

This invention was developed with federal support from the National Science Foundation, contract No. ATM-9871192.

BACKGROUND

Atmospheric scattering of light in the visible and near-visible spectral regions influences the earth's climate by changing short wave radiative forcing and influences optical remote sensing by ground-based, airborne, and satellite systems, including visual perception by humans. Scattering by particle free air is due to its gaseous components and seems to be well understood. The contribution of suspended particles to atmospheric scattering is highly variable in space and time and generally dominates the total extinction in the visible near the earth's surface.

Particle scattering is commonly characterized by integrating nephelometers that measure the scattering component of extinction also known as the total scattering coefficient. The necessary integration of the scattered light over all angles (i.e., $4\pi$) is performed geometrically with one of two schemes devised by Beuttell. Either a cosine-law diffuse light source is used to illuminate the scattering volume that is viewed with a detector, or detector and light source are reversed and a parallel light beam is used and the scattered light is detected by a cosine detector. The first arrangement is more common, and the second arrangement is known as reciprocal nephelometer. Calibration is generally performed with two gases that have a large difference in scattering coefficients such as air and carbon dioxide.

An ideal integrating nephelometer provides, after calibration, a direct measurement of the total scattering coefficient of suspended particles independent of their properties such as size, composition, and physical state. Real integrating nephelometers fall short of this ideal mostly due to imperfect angular and wavelength response and imperfect particle sampling.

Imperfect angular response arises because illumination intensity or detector sensitivity should be cosine-weighted but is not. In particular, light scattered at angles smaller than about 7° and larger than about 170° is not detected by modern nephelometers. These angles are known as truncation angles. As the angular distribution of particle scattering is strongly dependent on particle size, the measured scattering coefficient depends on this property. For the special case of very large particles, at least half of the scattered light is due to diffraction that is scattered in near-forward direction and may not be detected.

Imperfect aerosol sampling results in an aerosol in the measurement volume of the nephelometer has different scattering properties than the ambient aerosol of interest. Sampling losses of large particles due to impaction and gravitational settling are common.

Imperfect wavelength response is due to the integration of particle scattering over a wavelength range, typically 40 nm for commercial nephelometers using a thermal light source. As the wavelength dependence of particle scattering is size and refractive index dependent, the measured scattering coefficient is not appropriate for the nominal wavelength but only for the wavelength range with appropriate weighting due to the combined spectral response of light source, detector, filter, and other optical elements.

DETAILED DESCRIPTION

A nephelometer is disclosed herein that uses an integrating sphere with attached truncation-reduction tubes to contain the sample volume and to integrate the scattered light. The disclosed nephelometer improves on the imperfect angular response by using an integrating sphere design with forward (backward) truncation angles of ≈1° (≈179°), it reduces sampling losses by employing a substantially straight vertical flow path, and it eliminates imperfect wavelength response by utilizing a narrowband laser as light source. A related design, using a homogeneously illuminated integrating sphere containing the sample and a view path through the sphere into a light trap is disclosed.

Figure 1:
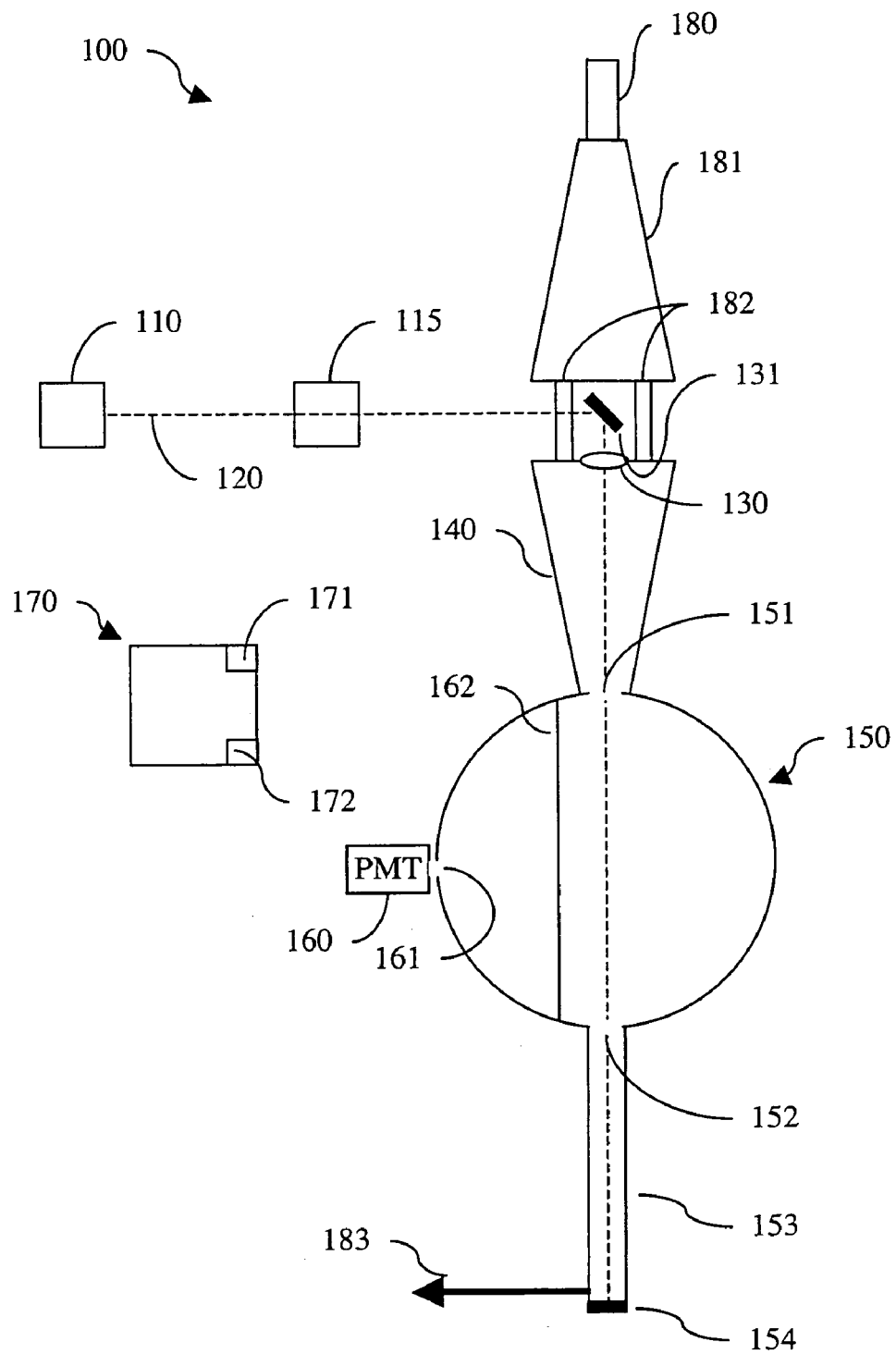
FIG. 1 is a diagram of an integrating nephelometer configured in accordance with the teachings of this disclosure.

Referring now to FIG. 1, a block diagram of an integrating nephelometer 100 configured in accordance with the teachings of this disclosure is shown.

The nephelometer 100 includes a light source 110. In a preferred embodiment, a frequency-doubled, all-solid-state, cw Nd:YAG laser 110 operating at 532 nm is used as light source. The beam is preferably chopped and spatially filtered in chopper and filter 115 to reduce wall scattering, and its power may be monitored as is known in the art.

An alternative, simpler embodiment uses an internally power-modulated Nd:YAG laser operating at 532 nm with single-mode fiber-coupled output. This implementation eliminates the mechanical chopper and the spatial filter. The single mode fiber acts as spatial filter and greatly simplifies setup and alignment.

The main beam 120 enters the forward truncation-reduction tube 140 and is directed towards the sphere 150 by mirror 131 through a window that may also act as lens 130, propagates through the integrating sphere's entrance aperture 151, its center, its exit aperture 152 and the backward truncation-reduction tube 153 into a beam trap 154. The laser beam exiting the spatial filter or fiber is either collimated or focused into the center of the integrating sphere 150 with its confocal parameter close to the sphere diameter d, thereby minimizing the beam diameter at the sphere's apertures.

In one embodiment, the integrating sphere 150 may be machined of solid aluminum with a diameter $d_0$=20 cm, and is segmented into two parts for easy access to its interior. Laser beam entrance 151 and exit 152 apertures of radius r (r=5 mm) are located on opposite poles of the sphere and truncation-reduction tubes of length $d_o$ are attached to each aperture.

A third aperture 161 of identical size is located on the equator of the sphere 150 with a photomultiplier tube (PMT) 160 attached. The inside surface of the sphere is coated with a highly reflecting (>99%) and near-Lambertian barium sulfate based coating. Laser light scattered by the medium in the sphere is integrated by multiple diffuse reflections in the sphere and consequently measured by the PMT 160. This third aperture may be disposed at any location on the body, but is preferably disposed behind a scattering baffle.

A 20-cm long, 1-cm wide baffle 162, also coated white, is mounted parallel to the laser beam to prevent light scattered by the medium from directly reaching the PMT.

As will be appreciated by those of ordinary skill in the art, the disclosed setup, minus truncation-reduction tubes, is similar to that used to measure the total scattering loss of optical fiber, with the fiber being replaced by the scattering medium. While the total area of the integrating sphere ports (entrance+exit+PMT aperture=2.4 cm$^2$) is very small (<0.2%) compared to the total inside surface of the sphere (0.13 m$^2$), loss of scattered light through the exit aperture can be significant for large particles, which scatter predominantly in the near-forward direction.

The light scattered in the integrating sphere is detected with the PMT 160, and its signal and the signal from the photodiode monitoring the laser power are acquired with an A/D converter as is known in the art. Both signals are measured with phase sensitive detection at the chopping frequency. The PMT signal is normalized to the laser power and can be converted into a scattering coefficient after instrument calibration. Ancillary data acquired include time, temperature, pressure, and relative humidity. Processing of the sampled data may be implemented in software residing in computer 170, which includes a processor 171 and associated memory for the execution of embodiments of this disclosure. The computer 170 may be operatively coupled to the various elements of the nephelometer 100 as required.

Inlet air is sampled from the top of FIG. 1 through a vertical 1.3-cm ID stainless steel tube 180 that can be switched under computer control between unfiltered and HEPA filtered. The inlet tube expands conically in section 181, is split into 4 individual 1.3-cm ID tubes (two of which are shown as tubes 182), which reunite and narrow down after coupling the laser beam into the center of the flow.

The flow enters and exits the integrating sphere 150 through its 1 cm diameter apertures 151 and 152 respectively, and terminates into the flow pump 183. The fairly straight vertical flow arrangement shown in FIG. 1 reduces particle losses due to gravitational settling and impaction.

An alternative implementation uses a transparent tube disposed within the integrating sphere with internal diameter equal to that of the ports to confine the sample flow within the integrating sphere. This improves flow properties (e.g., less turbulence, faster aerosol exchange and thereby faster time response) of the nephelometer. The transparent tube should be anti-reflection coated to prevent deterioration of the optical properties of the nephelometer.

The nephelometer of this disclosure may been calibrated with two independent, primary calibration schemes. In a first embodiment, a common method of calibrating nephelometers with two gases with different and well-known scattering coefficients ($CO_2$ and HEPA-filtered air) may be employed. Alternatively, in a second embodiment introduction of a plate with near-Lambertian and well-known reflectivity $R_C$ blocking the exit aperture of the integrating sphere in conjunction with a reduction in laser power by a neutral density filter with an optical density OD. The latter scheme is related to one described previously. The measured signal in the latter case corresponds to a scattering coefficient of $10^{-OD}R_C/d_0$. Results from both calibration schemes agreed within the measurement error. Initial comparisons of the disclosed integrating nephelometer with two other nephelometers (TSI 3563 and Radiance Research M903) using sub-micron particles revealed excellent correlation and agreement within a few percent. Comparisons with the M903 nephelometer during a study of dust entrainment by military off-road vehicles from an unpaved roadway, showed good agreement for ambient fine particles (no entrainment) while the nephelometer readings were up to four-times higher than those of the M903 for freshly entrained coarse particulate matter. This large discrepancy is attributed to the improved angular response, including a reduction of the truncation error by up to a factor of two, and the improved large particle sampling of the disclosed nephelometer compared to the M903.

Figure 2:
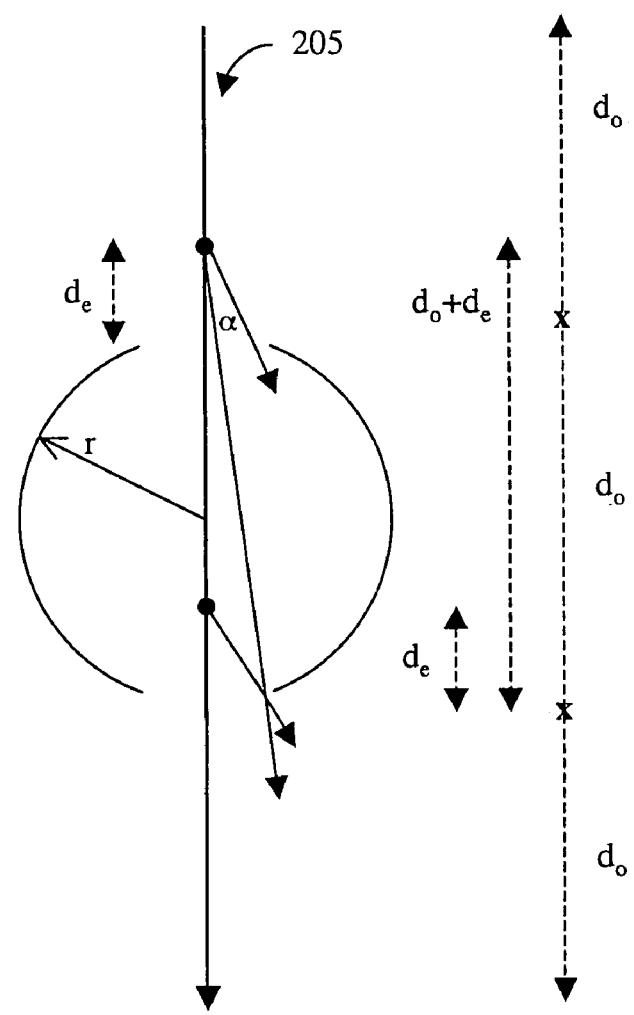
FIG. 2 is a diagram illustrating the loss truncation loss feature of nephelometers of this disclosure.

FIG. 2 is a diagram illustrating the low truncation loss feature of the disclosed nephelometer. The following discussion centers on the primary innovation provided by the disclosed nephelometer, the low truncation loss feature. The disclosed nephelometer geometry is symmetric in respect to forward and backward scattering truncation losses. However, truncation losses are only significant for large particles and in this case forward scattering losses dominate backward losses by a large amount. Therefore, this discussion is limited to forward truncation losses but can also be applied to backward losses.

Referring to FIG. 2, consider the case of only an integrating sphere filled with the scattering medium and with circular entrance and exit apertures of radius r. A laser beam 205 propagates along the sphere axis and is scattered by the scattering medium. The forward truncation angle $\alpha$ depends on the distance de from the scattering location in the sphere to the exit aperture as $\alpha_e = \tan^{-1}(r/d_e)$ and varies from 1.4° to 90° with an average of 6.7°.

To better confine the angles of both forward and backward truncation, truncation-reduction tubes of length $d_o$ are attached to each aperture and filled with the scattering medium. Now for each location at a distance $d_e$ from the exit aperture with a truncation angle $\alpha(d_e) = \tan^{-1}(r/d_e)$, there exists a location $d_0 + d_e$ in the truncation-reduction tube at a distance $d_e$ from the entrance aperture from which near-forward scattered light at angles smaller than $\alpha(d_e) = \tan^{-1}(r/d_e)$ enters the integrating sphere, compensating for the forward truncation loss of the sphere alone. However, this compensation is not complete as the central portion of the light near forward scattered into the sphere leaves it through its exit aperture. This yields an effective truncation angle of $\alpha(d_e + d_0) = \tan^{-1}(r/(d_e + d_0))$ that varies from 0.7° to 1.4°, with an average of 1.0°. Longer truncation-reduction tubes or smaller apertures could further reduce these truncation angles. Thus, the truncation tubes of this disclosure may be described as having lengths on the order of the diameter of the integrating sphere, but may comprises other lengths as desired.

For large particles, the truncation error can be approximated by diffraction theory and scales with x sin($\alpha$) or for small truncation angles $\alpha$ with (x $\alpha$), where x is the size parameter, the ratio of particle circumference and wavelength. Therefore, a reduction of the truncation angle from 7° to 1° allows detection of scattering from approximately 7-times larger particles with identical truncation error.

For example, a truncation error of larger than 25% occurs for non-absorbing (absorbing) particles at diameters larger than about 16 λm (11 μm) for a truncation angle of 1°, and for diameters larger than about 2.3 μm (1.4 μm) for a truncation angle of 7°. Strongly absorbing particles in the atmosphere are generally black carbon combustion products with sub-micron particle diameters, which do not contribute much to truncation errors. For non-absorbing particles, a nephelometer with a truncation angle of 7° loses a substantial part (i.e., >25% at d>2.3 μm) of scattering from the coarse particle mode, while the disclosed nephelometer with a truncation angle of 1° measures nearly all scattering from atmospheric aerosol. The 25% cutoff for the disclosed nephelometer occurs at 16 μm where the gravitational settling velocity ($\approx 0.8$ cm/s for a density of $\approx 1$ g/cm$^3$) is nearly a factor of 50 ($\approx (16/2.3)^2$) larger than at 2.3 μm and where most particles are removed from the atmosphere in a matter of hours.

While the utility of the truncation reduction tubes has been discussed here in the context of a reciprocal nephelometer, the same concept can be applied to a non-reciprocal nephelometer. In this case, a diffuse light source, for example a thermal light source or a Light Emitting Diode (LED) combined with a diffuser, takes the place of the detector generating a homogeneous illumination inside the integrating sphere. The laser light source is replaced with a detector (e.g., PMT) with imaging optics so that the black beamtrap located on the opposite side of the sphere and the illuminated medium between detector and beamtrap both within the sphere and within the truncation reduction tubes is imaged onto the detector. Without a sample, no light is scattered onto the detector, with the possible exception of wall scattering. With a sample filling the integrating sphere, light is scattered onto the detector, thereby generating a signal. Again, the forward and backward illumination angles of sample contained within the sphere are limited by the "dark" entrance and exit aperture.

The resulting truncation is largely compensated for by sample within the truncation reduction tubes allowing small forward scattering angles (near zero degree) and large backward scattering angles (near 180 degree) to contribute to the detector signal to reduce the truncation angles to within 1 degree of the forward and backward scattering directions.

Figure 3:
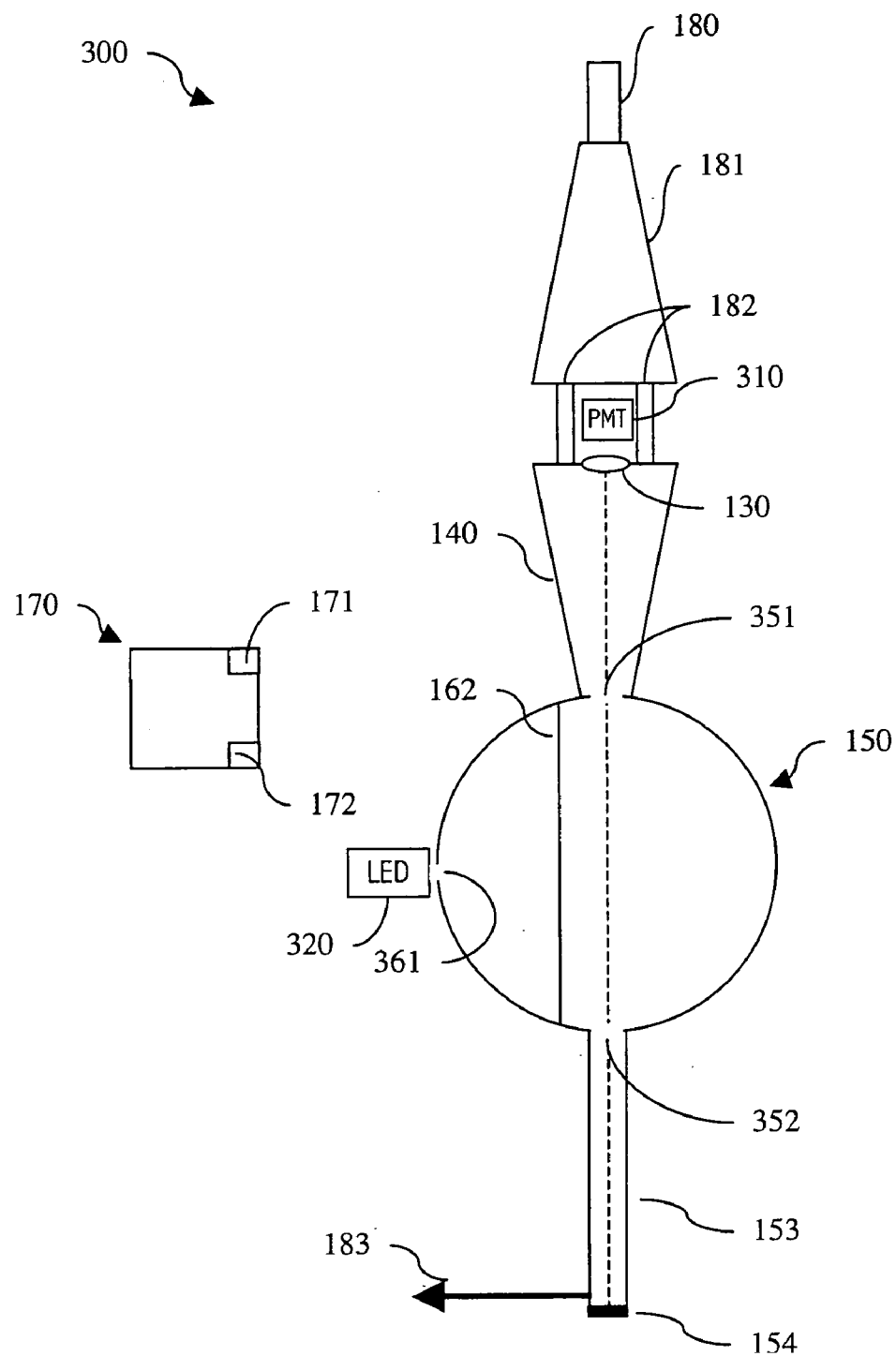
FIG. 3 is a diagram of a non-reciprocal nephelometer configured in accordance with the teachings of this disclosure.

FIG. 3 is a diagram of such a non-reciprocal nephelometer 300 configured in accordance with the teachings of this disclosure.

Figure 4:
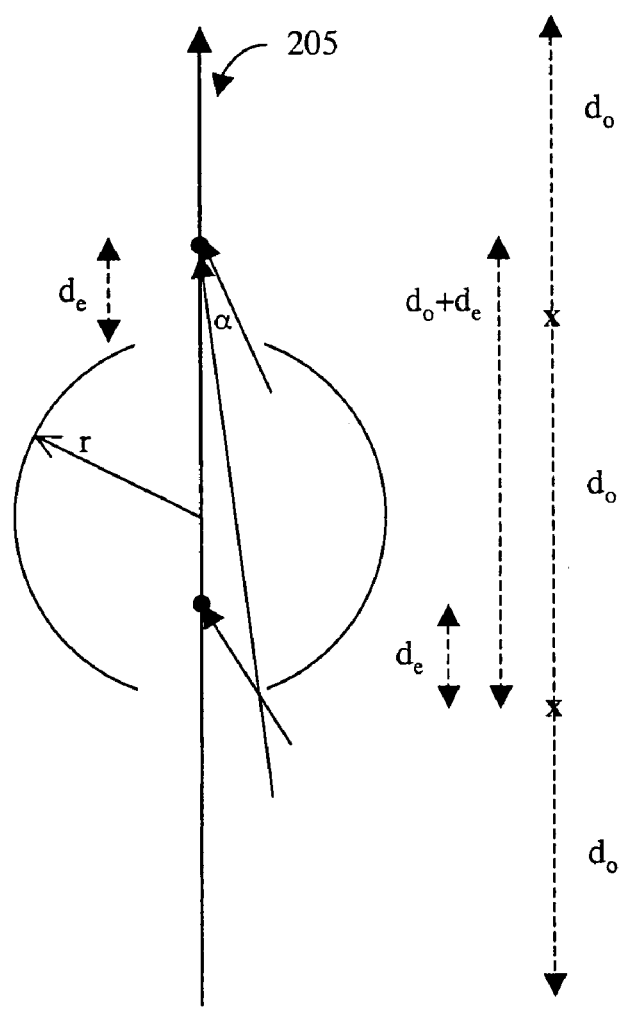
FIG. 4 is a diagram illustrating the truncation loss for a non-reciprocal nephelometer in accordance with the teachings of this disclosure.

The nephelometer 300 includes much of the structure of the nephelometer 100 of FIG. 1, however, the illumination source 320 and the detector 310 have been switched in place. Referring briefly to FIG. 4, a diagram illustrating the truncation loss for a non-reciprocal nephelometer embodiment is shown, with the direction of the scattering rays being reversed accordingly. The discussion below will discuss FIGS. 3 and 4 in view of the particularities of the non-reciprocal embodiment. Because the detector 310 is now located in-line with the sphere's axis, optical mirrors and other guidance structure has been omitted. The apertures now have different functions, with an illumination aperture 361 admitting light from the light source, the sensing aperture 351 admitting scattered light to the optical detector, and the dark aperture 352 providing a dark background viewing area for the optical detector.

Light source 320 is labeled as "LED" and preferably comprises an illumination assembly consisting of one or multiple diffuse light sources for homogenously illuminating the integrating sphere. Light sources can consist of thermal light source(s) or Light Emitting Diode(s) (LED(s)). LEDs have the advantage that they can be power modulated at relatively high frequencies (compared to thermal light sources) facilitating the suppression of ambient light through phase-sensitive detection (e.g., lock-in amplifier or Fast Fourier Transform).

The light source 320 may be made diffuse by either mounting a diffuser (e.g., opal glass filter) in front of it or by mounting it in a second integrating sphere to yield a diffuse light source. The light source is shown as illuminating the main integrating sphere and the view path in the truncation reduction tubes.

If multiple light sources at different wavelengths are employed, scattering coefficients can be measured at these corresponding wavelengths, for example in the blue (e.g., 450 nm), green (e.g., 550 nm) and red (e.g., 650 nm). In this case, each light source emits in a certain wavelength band defined by the light source and/or a spectral filter in front of the light source. The output power of each individual light source is modulated differently, for example, at a different modulation frequency. This way, a single detector can be used simultaneously for multiple wavelengths. The detector signal is analyzed, for example with respect to modulation frequency by lock-in amplifiers or by Fast-Fourier-Transform (FFT) analysis, to separate the scattering signal from the different wavelength source from each other and from background signals.

The detector assembly 310, labeled "PMT" in the drawing, preferably comprises a sensitive optical detector (e.g., a photomultiplier tube or PMT) and a lens or lens-assembly that images the dark interior of the light trap onto the detector. If the ISIN is evacuated, the detector signal would ideally be zero. In reality, there is always a small background signal due to wall scattering and/or some residual light coming from the light trap.

If a medium is introduced into the ISIN and more specifically into the view path, it scatters light into the detector assembly. Particles within the integrating sphere are illuminated by the light reflected from the interior walls of the sphere, that is from most directions with the exception of the sensing aperture 351 and the dark aperture 352. The forward truncation angle α depends on the distance $d_e$ from the scattering location in the sphere to the dark aperture 352 as $\alpha_e = \tan^{-1}(r/d_e)$ and varies from 1.4° to 90° with an average of 6.7°.

To better confine the angles of both forward and backward truncation, truncation-reduction tubes of length $d_o$ are attached to sensing and dark apertures 351 and 352 and filled with the scattering medium. Particles in these truncation-reduction tubes are illuminated from the integrating sphere to provide most of the missing near-forward and near-backward scattered light to the detector assembly. This process is symmetric for forward and backward truncation and is described in the following for forward truncation. Using truncation reduction tubes, for each location within the integrating sphere at a distance $d_e$ from the dark aperture 352 with a truncation angle $\alpha(d_e) = \tan^{-1}(r/d_e)$, there exists a location $d_0 + d_e$ in the truncation-reduction tube at a distance de from the sensing aperture 351 from which near-forward scattered light at angles smaller than $\alpha(d_e) = \tan^{-1}(r/d_e)$ is provided to the detector assembly, compensating for the forward truncation loss of the sphere alone.

However, this compensation is not complete as a particle at location $d_0 + d_e$ is not illuminated from the outside of the dark aperture 352, that is from the outside of the integrating sphere. This yields an effective truncation angle of $\alpha(d_e + d_0) = \tan^{-1}(r/(d_e + d_0))$ that varies from 0.7° to 1.4°, with an average of 1.0°. Longer truncation-reduction tubes or smaller apertures could further reduce these truncation angles.

The advantage is that we can use an LED light source (cost of a few dollars or less) instead of a laser light source (cost of a few thousand dollars)

We claim:

1. A nephelometer comprising:
    an integrating cavity body having a sensing aperture and a dark aperture opposite said sensing aperture disposed along a longitudinal axis and a third illuminating aperture disposed on said cavity body;
    a forward truncation-reduction tube coupled to said sensing aperture, said forward truncation-reduction tube configured to provide a scattering medium flow and scattered light from the cavity body and truncation reduction tubes to said sensing aperture;
    a light source disposed proximate to said illuminating aperture for providing a light source for said cavity body;
    a backward truncation-reduction tube coupled to said dark aperture configured to provide a dark background viewing area for the photomultiplier sensor and an exit for said scattering medium flow;
    said forward and backward truncation reduction tubes having a length on the order of the diameter of said cavity body; and
    a photomultiplier sensor operatively disposed proximate to said sensing aperture for sensing the scattering of said diffuse light source by said scattering medium within said cavity body and said forward and backward truncation reduction tubes.

2. The nephelometer of claim 1, wherein said integrating cavity body comprises an integrating sphere.

3. The nephelometer of claim 2, wherein the length of said forward and backward truncation reduction tubes is substantially equal to the diameter of said integrating sphere.

4. The nephelometer of claim 3, wherein the size of said sensing and dark apertures are chosen such that near-forward scattering occurring within said forward truncation tube substantially compensates for the forward truncation loss of said integrating sphere.

5. The nephelometer of claim 4, wherein the flow of said scattering medium through said truncation tubes and said cavity body occurs along a substantially straight path.

6. The nephelometer of claim 5, wherein said light source comprises an LED or thermal light source.

7. The nephelometer of claim 6, wherein the interior of said sphere is coated with a highly reflecting material such that light introduce through the illumination aperture is homogenized by multiple diffuse reflections within said sphere.

8. The nephelometer of claim 7, further comprising a baffle disposed within said sphere parallel to the path of said light source for preventing light from the illumination aperture from directly reaching said volume with the cavity body and truncation tubes that is viewed by the photomultiplier sensor.

9. A nephelometer comprising:
    integrating cavity body means having a sensing aperture and a dark aperture opposite said sensing aperture disposed along a longitudinal axis and a third illumination aperture disposed along an equatorial axis of said cavity body;
    forward truncation-reduction means coupled to said sensing aperture, said forward truncation-reduction means configured to provide a view path for the photomultiplier sensor and a scattering medium flow to said sensing aperture;
    backward truncation-reduction means coupled to said dark aperture, said backward truncation-reduction means configured to provide a dark viewing area for the photomultiplier sensor and an exit for said scattering medium flow;
    said forward and backward truncation reduction means having a length substantially equal to the diameter of said cavity body means; and
    sensor means operatively disposed within said sensing aperture for sensing the scattering of said diffuse light source by said scattering medium within said cavity body and said forward and backward truncation reduction tubes.

10. The nephelometer of claim 9, wherein said integrating cavity means comprises an integrating sphere.

11. The nephelometer of claim 10, wherein the length of said forward and backward truncation reduction means is substantially equal to the diameter of said integrating sphere means.

12. The nephelometer of claim 11, wherein the size of said sensing and dark apertures are chosen such that near-forward scattering occurring within said backward truncation tube substantially compensates for the forward truncation loss of said integrating sphere.

13. The nephelometer of claim 12, wherein the flow of said scattering medium through said truncation tubes and said cavity body occurs along a substantially straight path.

14. The nephelometer of claim 13, wherein said light source comprises a light emitting diode (LED) or thermal light source.

15. The nephelometer of claim 14, wherein the interior of said sphere means further comprises means for homogenizing the light from the illumination aperture within said sphere.

16. The nephelometer of claim 15, further comprising baffle means source for preventing light from the light source from directly reaching the view path of said sensor, said baffle means disposed within said sphere parallel to the path of said light.

17. The nephelometer of claim 3, wherein the size of said sensing and dark apertures are chosen such that near-backward scattering occurring within said backward truncation tube substantially compensates for the backward truncation loss of said integrating sphere.

18. The nephelometer of claim 11, wherein the size of said sensing and dark apertures are chosen such that near-backward scattering occurring within said backward truncation tube substantially compensates for the backward truncation loss of said integrating sphere.

* * * * *